(12) United States Patent
Schweizer et al.

(10) Patent No.: US 6,223,077 B1
(45) Date of Patent: Apr. 24, 2001

(54) AUTOMATIC POWER SWITCHING IN A DEFIBRILLATOR

(75) Inventors: Scott O. Schweizer, Snohomish; Gus H. White, Redmond; Aaron Huynh, Bothell, all of WA (US)

(73) Assignee: Physio-Control Manufacturing Corporation, Redmond, WA (US)

( * ) Notice: Subject to any disclaimer, the term of this patent is extended or adjusted under 35 U.S.C. 154(b) by 0 days.

(21) Appl. No.: 09/013,142

(22) Filed: Jan. 26, 1998

(51) Int. Cl.[7] .................................................. A61N 1/39
(52) U.S. Cl. ................................................ 607/5; 607/29
(58) Field of Search ................................. 601/5, 6, 29, 9

(56) References Cited

U.S. PATENT DOCUMENTS

| | | |
|---|---|---|
| 4,323,075 | 4/1982 | Langer . |
| 5,063,928 | 11/1991 | Grevis et al. . |
| 5,292,348 | 3/1994 | Saumarez et al. . |
| 5,470,341 | 11/1995 | Kuehn et al. . |
| 5,611,815 | 3/1997 | Cole et al. . |
| 5,674,252 | 10/1997 | Morgan et al. . |
| 5,690,685 | 11/1997 | Kroll et al. . |
| 5,868,794 * | 2/1999 | Barkley et al. .......................... 607/29 |

OTHER PUBLICATIONS

Selected pages from LIFEPAK 11 Defibrillator/Pacemaker Service Manual, Jan. 1995.
Linear Technology LTC 1479 Data Sheet, 1996.

* cited by examiner

*Primary Examiner*—George R. Evanlsko
(74) *Attorney, Agent, or Firm*—Christensen O'Connor Johnson Kindness PLLC

(57) ABSTRACT

A method and apparatus for providing automatic power switching in a portable external defibrillator is disclosed. The power supply switching circuit includes a plurality of power supply ports for receiving power sources such as batteries and external power sources. The power supply switching circuit works with both batteries that include monitoring devices (smart batteries) and batteries that do not include monitoring devices (dumb batteries). The power supply switching circuit also includes microprocessor controllable switches for selectively coupling the power supply ports to the output of the power supply switching circuit, and a microprocessor for controlling the switches and for monitoring the power supply ports. Resident in the microprocessor is a control program for controlling the switching and monitoring operations. The control program uses data received from the power sources to select the best available power source to be used as the output for the power supply switching circuit. The control program has routines for monitoring both smart and dumb batteries, and the power supply switching circuit can thus use a combination of smart and dumb batteries. In one test, a load is placed on a battery and then the output voltage of the battery is measured. A user of the defibrillator is kept completely informed as to the status of the power sources through information that is provided from a display or auditory signals. For smart batteries, a fuel gauge is provided on the display. Warnings are provided when a battery needs changing, or when other user action is required.

30 Claims, 6 Drawing Sheets

AUTOMATIC POWER SWITCHING IN A DEFIBRILLATOR

FIELD OF THE INVENTION

This invention relates generally to methods and apparatus for providing power to a cardiac defibrillator and, more specifically, to switching between various available cardiac defibrillator power sources.

BACKGROUND OF THE INVENTION

Batteries are often used to power portable electronic defibrillators. Portable defibrillators generate and apply a high-energy defibrillation pulse to the chest of a patient to cause the patient's heart to stop fibrillating and return to a normal rhythm. The pulses require high energy levels (up to 360 joules) and sometimes multiple defibrillation pulses are required to restore the patient's heart to a normal rhythm. Thus, defibrillators require large amounts of power during normal use. Because of the power requirements, portable external defibrillators generally use special battery packs to power the defibrillator. If the batteries that are being used by the defibrillator become depleted, the patient cannot be treated.

The power supply needs for portable defibrillators are distinct from many other portable devices in that the precision and urgency required is much greater, because a patient's life is often at stake. Urgency is often required because the chances that a patient's heart can be successfully defibrillated increase significantly if a defibrillation pulse is applied quickly. Thus, it is important that a defibrillator be able to resolve any power supply problems quickly with a minimum of distraction to the user.

Due to the critical nature of the power supply, some portable defibrillators have been equipped with backup batteries. Such defibrillators allow an operator to switch to the backup batteries if the original batteries fail. In the past, such systems have usually required the user to manually set switches to select one of the alternate power sources. Such systems have also required the user to manually track the battery maintenance with a gauge or other device. It is difficult in such systems for a user to keep track of which power source is most appropriate for use and when to switch from one source to another without affecting unit operation.

One particular problem is that switching of the power supply in a defibrillator can interrupt critical functions, such as monitoring of the patient's heart and the charging of the circuitry in preparation for applying a defibrillation pulse. Also, many defibrillators have special safety systems that monitor for out-of-tolerance voltages in the system and trigger a reset when out-of-tolerance voltages occur. Thus, power switching in such systems can accidentally trigger the safety reset of the system.

Some prior implantable defibrillators have attempted to address some of the power supply issues of defibrillators. One such device is shown in U.S. Pat. No. 4,323,075 to Langer, which discloses a method for battery failure compensation for a power supply used in an implantable defibrillator. As shown in FIG. 2 of Langer, a pair of batteries B1 and B2 are connected in series to provide the power for the defibrillator circuit. Two diodes, D1 and D2, are connected in parallel with each of the batteries B1 and B2, respectively. As described, one of the problems with the circuit is that if one of the batteries connected in series goes "dead," the current output by the series of batteries is limited by the output of the dead battery. This presents a serious problem in a defibrillator where a high current is often needed to charge the capacitor that provides energy for the defibrillation pulse. While one solution to this problem would be to provide switches for bypassing a dead battery, this solution is unacceptable because it drops the voltage of the series batteries by removing the voltage provided by the "dead" battery. Even a "dead" battery that is unable to deliver sufficient current is usually capable of adding at least some voltage to the overall level of the series battery circuit. The voltage provided by the dead battery, in addition to the voltage provided by the good battery(s), are often both required to operate a fibrillation detection circuit. In Langer, the diodes D1 and D2 allow the necessary current requirements for the charging circuit to be met by bypassing the current around a dead battery, while still allowing the voltage level from the dead battery to be included in the circuit for operating the fibrillation detection circuit.

Other implantable defibrillators have attempted to address the need to generally monitor the life of a defibrillator battery so that some warning can be given before the battery is completely drained. Such a device is shown in U.S. Pat. No. 5,292,348 to Saumarez et al., which discloses an implantable cardioverter/defibrillator and method employing cross-phase spectrum analysis for arrhythmia detection, and also in U.S. Pat. No. 5,063,928 to Grevis et al., which discloses an apparatus and method for detecting and treating cardiac tachyarrhythmias. Both of these patents show a power supply, such as a battery, and a signal line for monitoring the battery's condition. The signal line provides an end of battery life (EOL) signal to a microprocessor. The EOL signal is a logic signal whose status is indicative of the approach of battery failure in the power supply.

Still other implantable defibrillators have addressed the issue of the need to perform automatic battery maintenance within a defibrillator. One such device is shown in U.S. Pat. No. 5,690,685 to Kroll et al., issued Nov. 25, 1997, which discloses an automatic battery-maintaining implantable cardioverter defibrillator and method for use. Kroll et al. describe a device and method for performing automatic battery maintenance as particularly applied to an implantable cardioverter defibrillator. Batteries are maintained at a predetermined state of charge by addressing a problem internal to the battery itself, specifically that over time batteries can develop a high internal impedance or equivalent series resistance. As described, the voltage, current or other parameter from the battery is monitored to determine if the state of charge value is too low, in which case a battery loading maintenance cycle is switched into activation until the state of charge value improves.

While the above devices do address some of the power supply issues that arise for defibrillators, they do not address the issues of how and when to switch to backup power supplies. Neither do they make use of the features of the new "smart" batteries that have been developed to provide measurements of their own internal parameters and thus indicate when battery failure is approaching. Nor are they easily upgradable to make use of new battery technologies as they develop.

The present invention is directed to providing a method and apparatus that overcome the foregoing and other disadvantages. More specifically, the present invention is directed to providing a method and apparatus for automatic power switching in a portable defibrillator that makes use of the most recently available battery technologies and is easily upgradable.

SUMMARY OF THE INVENTION

In accordance with this invention, an automatic power switching method and apparatus is provided. The apparatus comprises an automatic power switching circuit that includes power supply ports for receiving power sources such as batteries and external power sources. The automatic power switching circuit also includes microprocessor controllable switches for selectively coupling the power supply ports to the output of the power supply. The automatic power switching circuit further includes a microprocessor coupled to the power supply ports and switches for monitoring the power sources and for selectively controlling the switches.

In accordance with one aspect of the invention, the microprocessor is controlled by a control program. The control program includes a selection routine for selecting a power supply port receiving power from a power source to be coupled to the output of the power supply. The selection routine evaluates data received from the power sources, and evaluates the data according to criteria that are desired for the operation of an external defibrillator. The selection routine includes a subroutine suitable for evaluating data received from smart batteries. Thus, the user need not be concerned with what the power source is and when to switch, as the microprocessor takes care of these considerations. Using the control program, the microprocessor is also able to perform selection of a power source within a predetermined time frame and with a level of precision that allows smooth and uninterrupted operation of the defibrillator.

In accordance with another aspect of the invention, the selection routine also includes a subroutine suitable for evaluating data received from non-smart or dumb batteries. This allows the power supply switching circuit to make use of both smart and non-smart batteries within a single device. This is especially advantageous in defibrillators, where special battery packs are often used, and the expense or non-availability of certain types of battery packs may make combined usage a requirement.

In accordance with another aspect of the invention, the control program detects when an external supply is available, and can use the external supply to power the defibrillator. The microprocessor also coordinates the charging of the batteries with the use of the external supply. Also, the selection routine of the control program includes a subroutine suitable for evaluating data received from a smart external power supply. Thus, a portable external defibrillator can be plugged or unplugged from an external power supply, and batteries can be used and replaced, with automatic power switching taking place so as to not affect or interrupt critical defibrillator operations. This is especially important in defibrillators, where rapid selection and use of the best available power source is critical, and where improper switching between power supplies may cause interruption of critical defibrillator operations. One particular type of critical interruption that may be avoided is the safety reset interruption that occurs when out of tolerance voltages are caused by improper power switching and thus cause the system to reset. The safety reset can cause capacitor charging and patient monitoring system reinitialization delays that are also thus avoided.

In accordance with another aspect of the invention, one of the tests for the batteries in the defibrillator consists of placing a load on them and attempting to draw a relatively high current (e.g. 1 amp). The output voltage of the battery is then also measured a short time later (e.g. after 200 milliseconds) to determine if it falls within a specified range (e.g. above 10.5 volts for a 12 volt battery). This type of test is especially important in defibrillators, where high currents and consistent voltage levels are needed for consistent and reliable defibrillator operation. The microprocessor is also able to determine when such tests are not need for certain smart batteries, which may provide such data without requiring the use of such tests.

In accordance with another aspect of the invention, the microprocessor uses a display and certain auditory tones to provide information to a user regarding the status of the power sources. Indications are provided when batteries are in need of maintenance or charging. In addition, a fuel gauge may be displayed on the display for smart batteries. Special routines are provided for testing and monitoring the power sources according to criteria that are desired for the operation of a portable device such as an external defibrillator. Thus, a user is kept completely informed as to the status of the power sources, and is prompted if action is needed. This is extremely advantageous in a defibrillator, where inattentiveness or lack of information regarding power supply problems can possibly render a defibrillator inoperable.

In accordance with another aspect of the invention, all of the power sources are switched and fused to a single common system power output. This requires fewer unit wires carrying large currents. Also, the electronic switching and the use of solid-state switches avoids the electromechanical failures of manual switches that were used in previous devices.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

The present invention is a method and apparatus for providing automatic selection and switching between various available power sources, and in particular batteries in a defibrillator that provides a defibrillation pulse to a patient's heart. Portable defibrillators may be powered by two or more batteries or by an external power source, when available. Rapid selection of the best available power source for a defibrillator with a minimum of distraction to a user is highly desirable because a defibrillation pulse must be applied to a patient both quickly and with enough energy. Otherwise the patient may be harmed.

Figure 1:
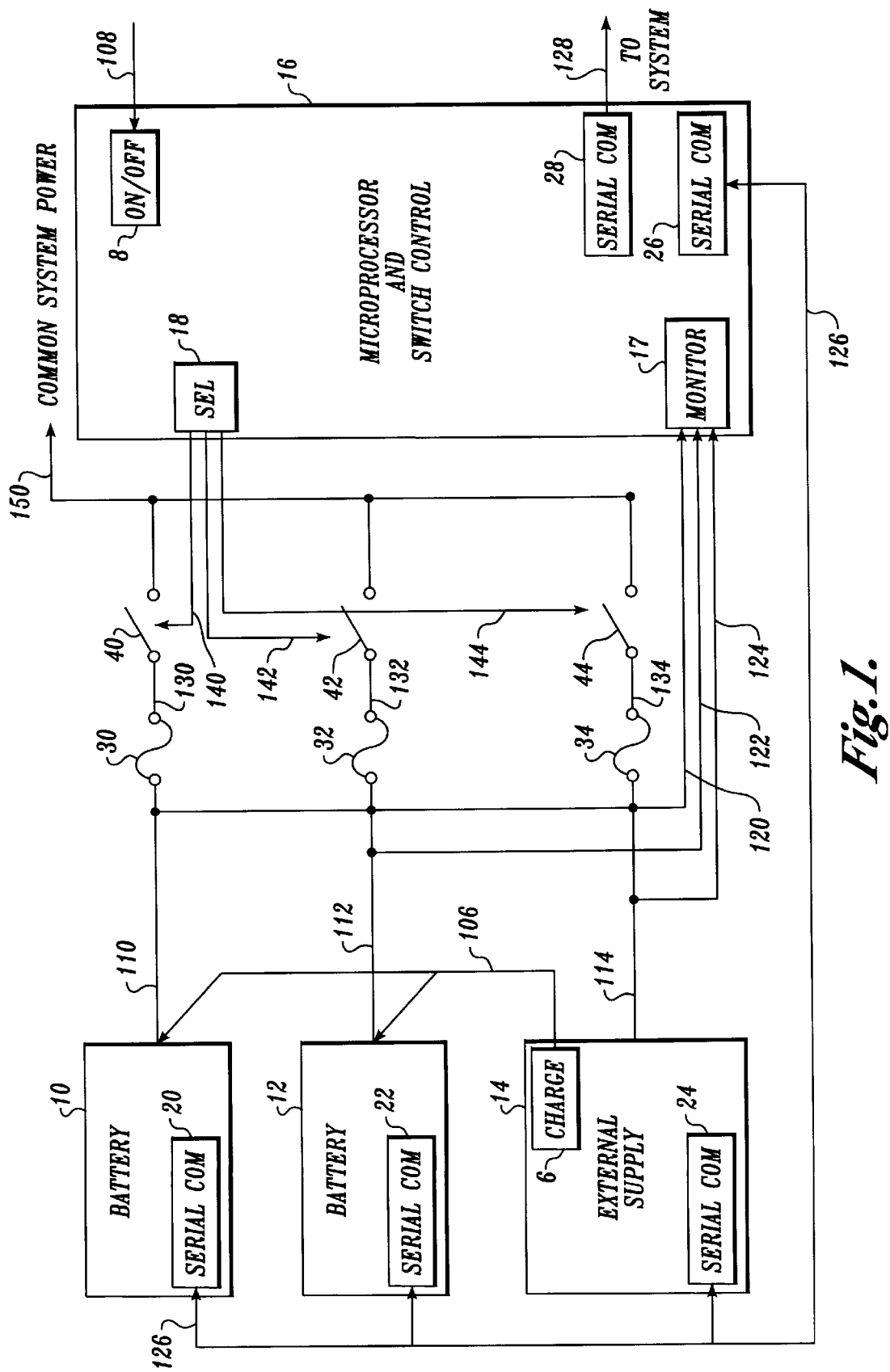
FIG. 1 is a block diagram of an automatic power switching circuit for use in a portable defibrillator according to the present invention.

A block diagram of an automatic power switching circuit formed in accordance with the present invention is illustrated in FIG. 1. The circuit includes two batteries 10 and 12, an external power supply 14, and a microprocessor and switch controller 16. As will be described more fully below, the microprocessor and switch controller 16 monitors the condition of the batteries 10 and 12, and the external supply 14, and uses the resulting data to select one of the power supplies as the power supply for the system. The external power supply 14 may not always be available. The nature of the external power supply 14 depends on the type of defibrillator being used. In a type of defibrillator which runs primarily off of DC battery power, the external power supply may be an external auxiliary supply that provides DC power but is itself powered by AC. In another type of defibrillator that runs primarily off of AC power with battery backup power, the external power supply may be a source such as a wall socket that provides AC power.

Batteries 10 and 12 each have serial communication ports 20 and 22, respectively. External power supply 14 has a serial communication port 24. External power supply 14 is a "smart" external auxiliary supply that includes monitoring circuitry to perform measurements regarding the auxiliary supply's condition (e.g., voltage and current output capacities), and to make the results of the measurements available to the microprocessor through its serial communication port. Batteries 10 and 12 are "smart batteries," i.e., batteries 10 and 12 are batteries that include monitoring circuitry to perform internal measurements as to the battery's condition (e.g., the battery's charge capacity, the level of stored energy, etc.) and make the results of the measurements available to the microprocessor through their serial communication ports. These measurements are sometimes referred to as providing a type of "smart fuel gauge" for the batteries. While batteries 10 and 12 are smart batteries, as will be described below, the system is also designed to obtain and process information from older non-smart or "dumb" batteries. The serial communication ports 20, 22, and 24 are coupled through a bus line 126 to a serial communication port 26 of the microprocessor and switch controller 16. Thus, microprocessor and switch controller 16 is able to monitor the condition of batteries 10 and 12 and external power supply 14 through the information provided from the serial communication ports 20, 22, and 24, respectively. Microprocessor and switch controller 16 also includes a serial communication output port 28 for providing data to the general defibrillator control circuit and display (not shown) through a line 128.

The power outputs for batteries 10 and 12 are coupled to lines 110 and 112, respectively. The power output for external supply 14 is coupled to a line 114. External power supply 14 also includes a port 6 for providing a charging output on a line 106 for charging the batteries 10 and 12. Microprocessor and switch controller 16 monitors the voltage on lines 110, 112, and 114 through lines 120, 122, and 124, respectively, connected to a monitor port 17. Thus, in the case where non-smart batteries are used in place of smart batteries 10 and 12, voltage measurements can still be taken by the microprocessor and switch controller 16 from the power outputs of the batteries on lines 110 and 112.

Output lines 110, 112, and 114 are coupled to lines 130, 132, and 134 through uses 30, 32, and 34, respectively. The outputs from the power sources are fused for fire safety. The lines 130, 132, and 134 are coupled through switches 40, 42, and 44, respectively, to a single common system power line 150. Preferably, the switches are solid state switches. Switches 40, 42, and 44 are controlled by control lines 140, 142, and 144, respectively, from a selection port 18 in microprocessor and switch controller 16, Microprocessor and switch controller 16 also includes an on/off switch 8 that is controlled by a line 108 from the defibrillator system.

Figure 2:
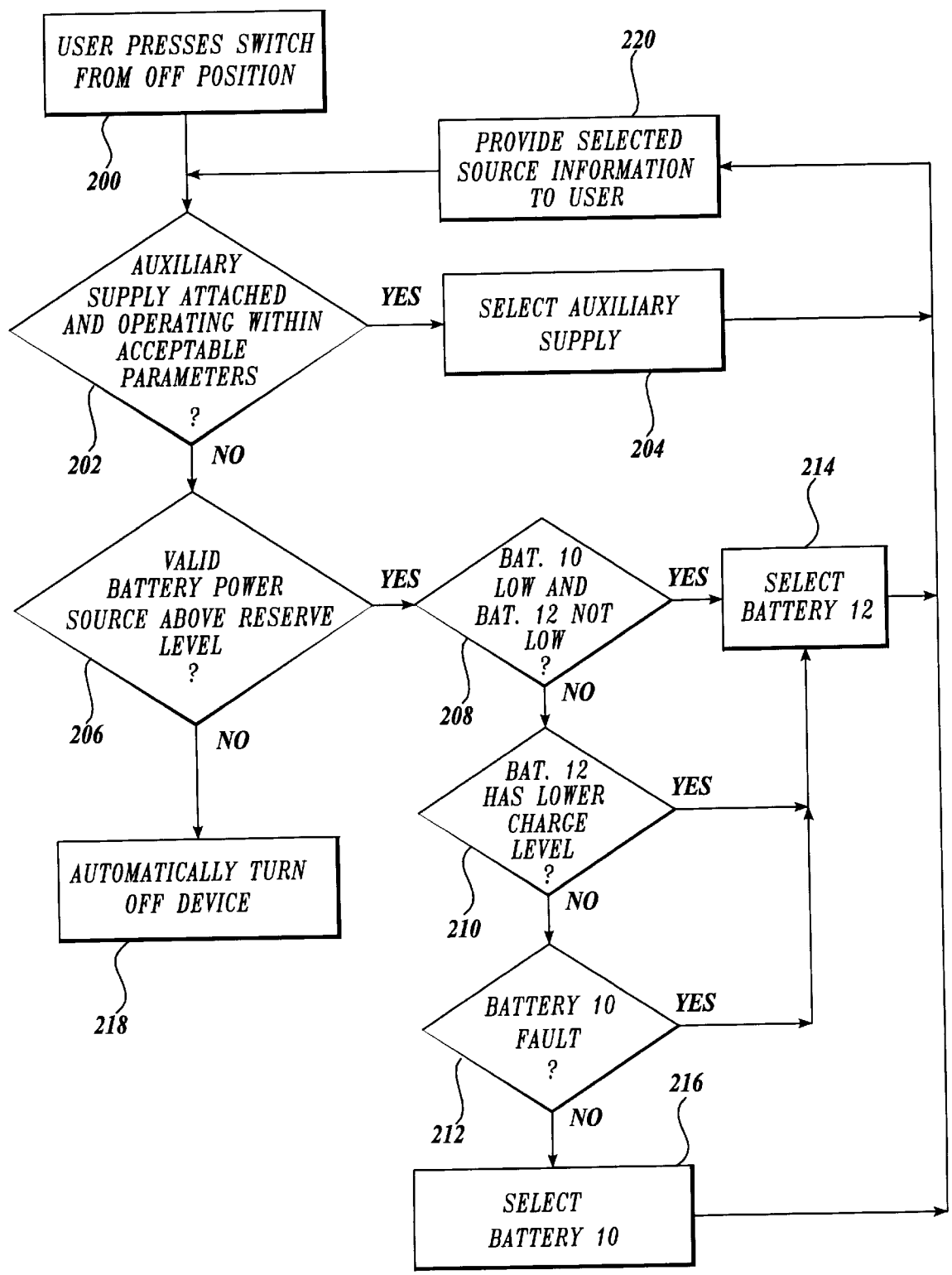
FIG. 2 is a flow chart illustrating the power supply selection method of the present invention.

FIG. 2 illustrates the power source selection operation of the automatic power switching circuit of FIG. 1. As shown at a block 200, the unit is first turned on by a user. At a decision block 202, the input power sources are sampled and evaluated for acceptable operating parameters. Specifically, the microprocessor and switch controller 16 checks to determine if an external (auxiliary) supply is attached and is operating within acceptable parameters. With reference to the circuitry of FIG. 1, this step is accomplished by the microprocessor and switch controller 16 checking lines 124 and 126 to determine if an external supply 14 is available. Although FIG. 1 is shown with external supply 14 included, it may often be disconnected when the portable defibrillator is being carried around, so that batteries 10 and 12 are the only power supplies available.

Returning to FIG. 2, if at decision block 202 the microprocessor 16 determines that an external (auxiliary) supply is available and is operating within acceptable parameters, the microprocessor proceeds to a block 204. At block 204, the microprocessor selects the external (auxiliary) supply as the defibrillator power supply. Thus, if an auxiliary supply is attached and is operating within acceptable parameters, it takes precedence over the other power sources and is selected to power the defibrillator. With reference to the circuitry of FIG. 1, the operation at block 204 is performed by the microprocessor and switch controller 16 closing switch 44 such that the output 114 from external power supply 14 is connected to the common system power line 150.

Returning to FIG. 2, if at decision block 202 the microprocessor determines that no external (auxiliary) supply is attached or, if attached, is not functioning properly, the microprocessor proceeds to a decision block 206. At decision block 206, the microprocessor monitors the available batteries to determine which batteries have power and their status (as will be described in more detail below with reference to FIGS. 3–6). With reference to the circuitry of FIG. 1, the operation at block 206 corresponds to the microprocessor evaluating batteries 10 and 12 for proper operating parameters. These operating parameters are based on the battery's ability to maintain voltage above minimum reserve levels while under a load. While performing this evaluation, the microprocessor and switch controller 16 monitors serial communications from serial communication ports 20 and 22 and/or monitors outputs 110 and 112 to determine if the batteries 10 and 12 meet the operating parameters. If the smart batteries 10 and 12 are replaced by non-smart batteries, the determination of the batteries' functionality is based on the measurements of the outputs 110 and 112. If there are no power sources available that meet the operating parameter requirements, the microprocessor proceeds to a block 218. At block 218, the power management software of the microprocessor automatically shuts off the power to the defibrillator.

At block 206, if the microprocessor determines that at least one of the battery power sources meets the proper operating parameters, the microprocessor proceeds to a decision block 208. The series of steps represented by blocks 208, 210, 212, 214, and 216 and described next comprise a routine run by the microprocessor that results in the selection of one of two batteries for use as the power source of the defibrillator. It will be understood that in a system that contains more than two batteries, similar testing techniques can be used to select the most appropriate battery.

At decision block 208, the microprocessor determines whether the power condition of the battery 10 is low and whether the power condition of the battery 12 is above low. For non-smart batteries in a 12-volt system, a low power condition is determined by measuring the output 110 or 112 of the battery to determine if it falls below a selected threshold (e.g., 10.5 volts). When smart batteries are being used, the low power condition is determined by monitoring the serial communication from ports 20 and 22 on line 126.

From decision block 208, if battery 10 has a low power condition while battery 12 does not have a low power condition, the microprocessor proceeds to a block 214. At block 214, the microprocessor and switch controller 16 selects battery 12 to supply power to the defibrillator. With reference to the circuitry of FIG. 1, the selection of battery 12 at block 214 corresponds to the microprocessor and switch controller 16 closing switch 42 and thus connecting the output 112 to the common system powerline 150.

If at decision block 208 the microprocessor determines that the power condition of battery 12 is low or that the power condition of battery 10 is not low, the microprocessor proceeds to a decision block 210. At decision block 210, the microprocessor determines if battery 12 has a lower charge level than battery 10. In the preferred embodiment, the status of the charge level is easily read from smart batteries, as this is one of the internal measurements they provide. The microprocessor will select the battery with the lower charge level to be used first. This is done so that the most depleted battery will be used first, thus allowing for the most efficient use of the batteries in the system. If at block 210 the microprocessor determines that the battery 12 has a lower charge level than battery 10, the microprocessor proceeds to block 214 where battery 12 is selected to power the system.

If at block 210 the microprocessor determines that the battery 12 does not have a lower charge level than battery 10, the microprocessor proceeds to a decision block 212. At decision block 212, the microprocessor determines whether battery IO has a fault. A fault condition is communicated by a smart battery when the smart battery monitoring circuitry determines that the smart battery has an internal fault. Alternatively, a fault can be generated from any type of battery if the path to the battery, such as the fuse or the switch, goes bad or if the battery is unable to support a charge when tested. An example of a battery unable to support a charge would be 12-volt battery that consistently drops to a 5-volt level when a load is placed on it. If battery 10 has a fault, then the microprocessor proceeds to block 214 where battery 12 is selected to power the defibrillator. If at block 212 the microprocessor determines that battery 10 does not have a fault, the microprocessor selects battery 10 to power the defibrillator.

From blocks 204, 214, and 216, the microprocessor proceeds to a block 220. At block 220, the microprocessor provides selected source information to a user on a display device, which the microprocessor communicates with via port 28 and communication line 128. The information about each of the power sources that is displayed to the user is described in more detail below with reference to FIG. 6. From block 220, the microprocessor returns to decision block 202 and another pass is made through the power supply selection procedures described above.

An additional feature of the invention is that it coordinates battery charging with the external supply 14, assuming the external supply 14 has serial communication capability. In this regard, the microprocessor and switch controller 16 monitors the status of the batteries 10 and 12 through serial communication ports 20 and 22 or through measurement lines 120 and 122 and determines when and how long the batteries should be charged by external supply 14.

In summary, the control program software routine of FIG. 2 causes the microprocessor and switch controller 16 to monitor the battery conditions and take appropriate action with regard to selecting a power source and charging the batteries. The selected battery is fully used until a defined switching point is reached. When this occurs, the next battery is selected. This allows complete use of battery power before switching, increasing unit operation time and battery life. As will be described in more detail below, all switching is automatic and is made known to the user through the system/user interface provided on the display device.

Figure 3:
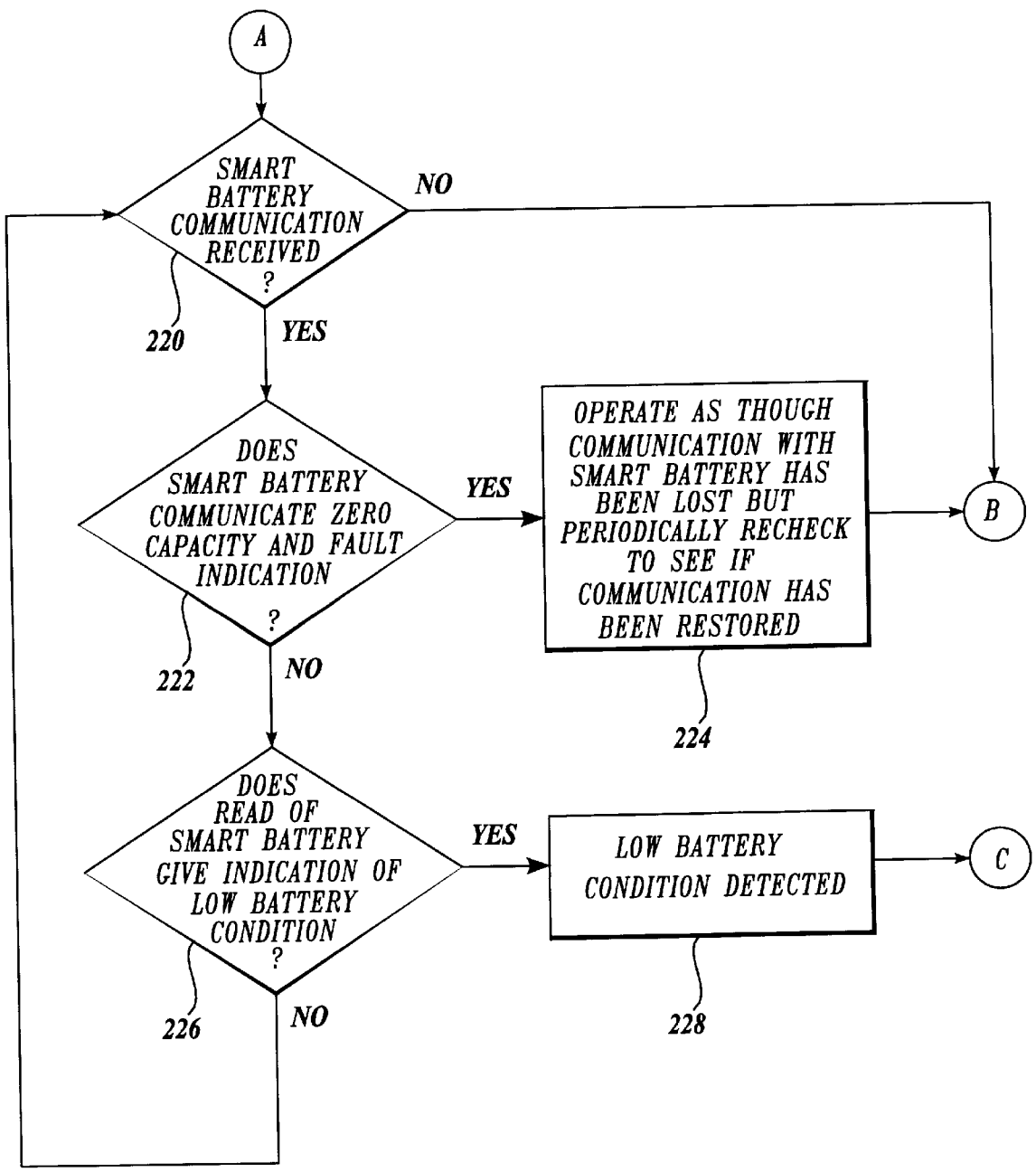
FIG. 3 is a flow chart illustrating a battery monitoring method for a smart battery.
Figure 4:
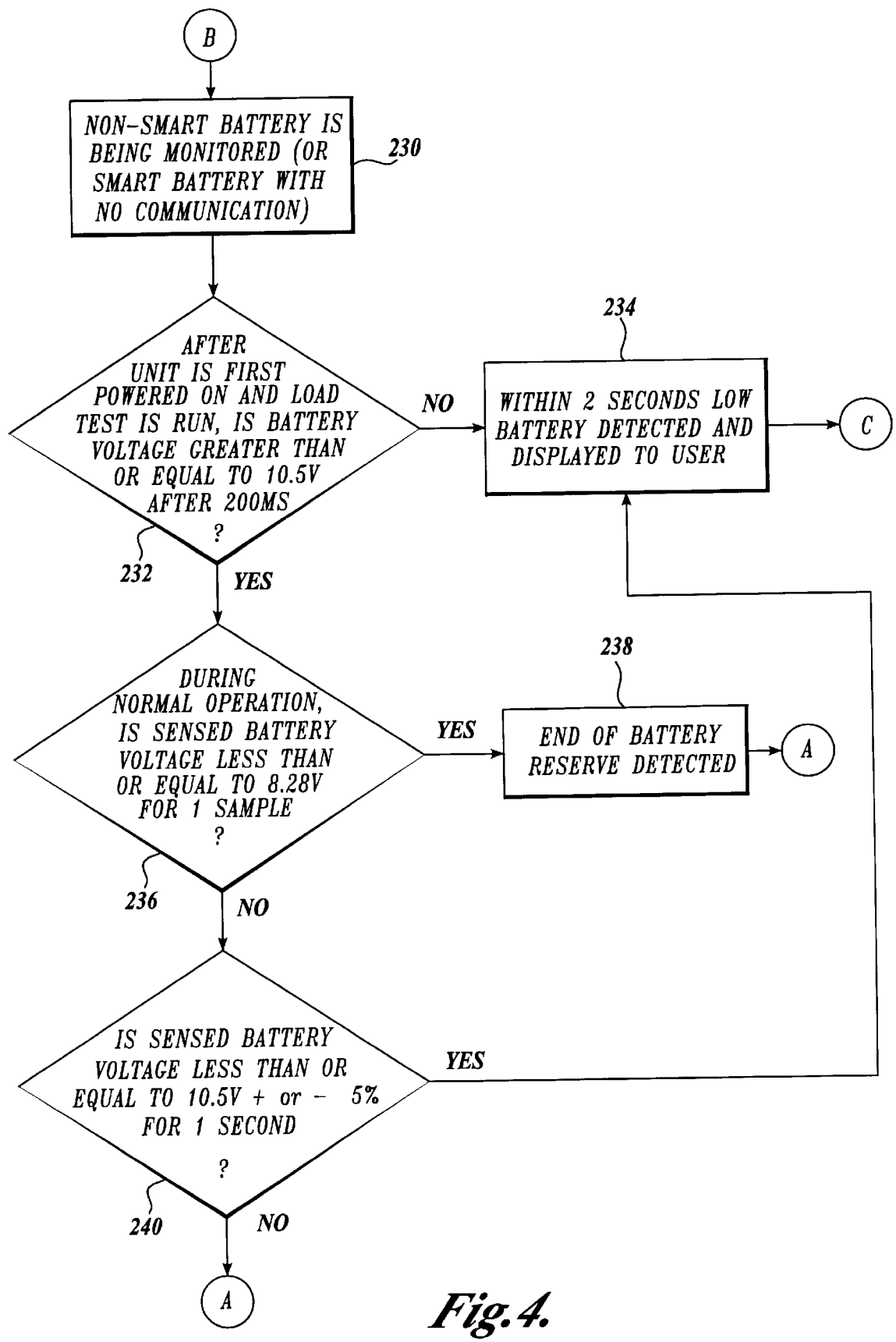
FIG. 4 is a flow chart illustrating a battery monitoring method for a non-smart battery.
Figure 5:
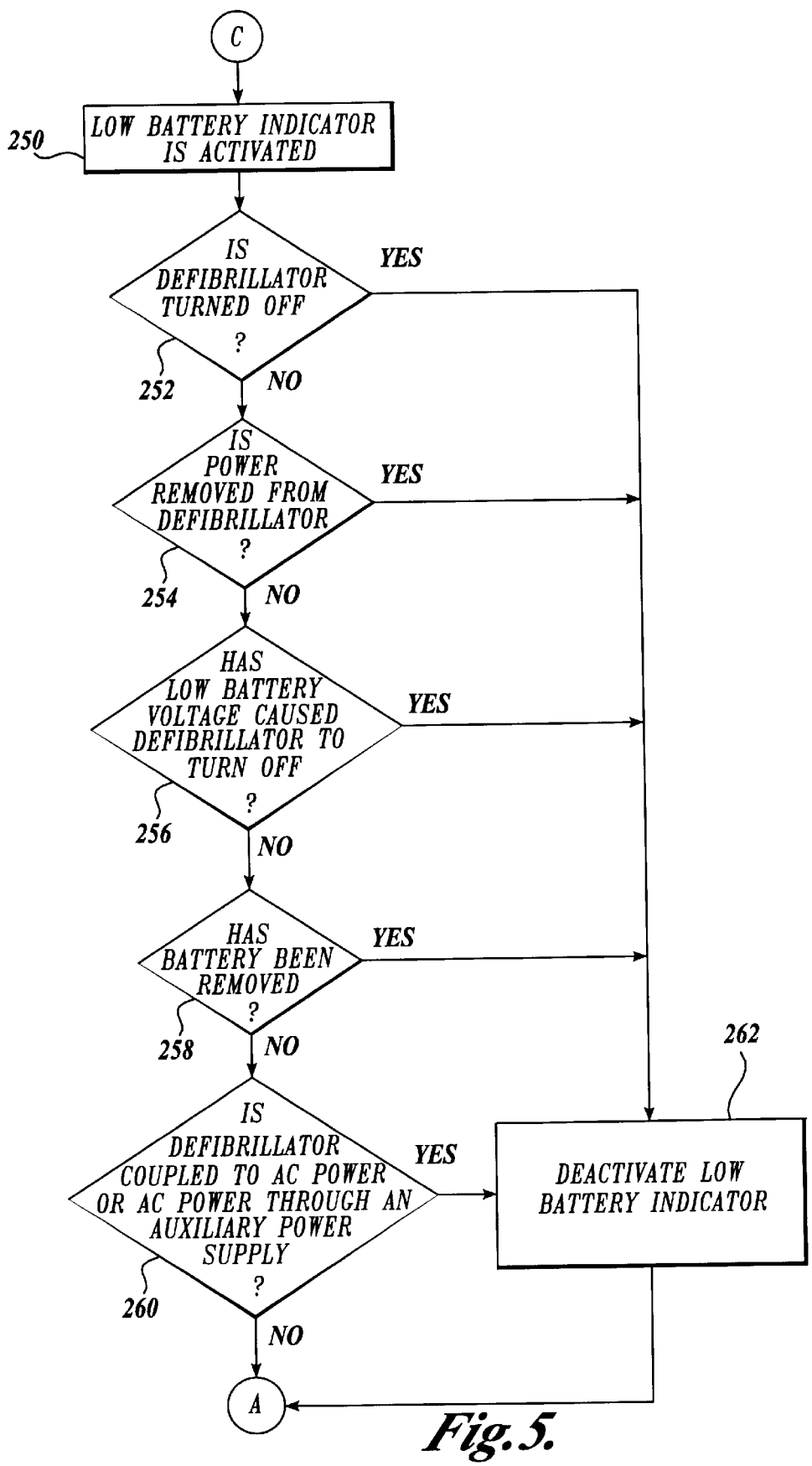
FIG. 5 is a flow chart illustrating a low battery indicator activation and deactivation method.

The above-described functions of the automatic power switching system of the present invention are described in more detail below with reference to FIGS. 3–6. FIGS. 3–5 generally illustrate the internal measurements and determinations made by the microprocessor and switch controller 16, while FIG. 6 generally illustrates the procedures for displaying information to a user of the device.

As illustrated in FIG. 3, battery monitoring, such as that required at block 206 of FIG. 2, begins at point A of FIG. 3. At a decision block 220, the microprocessor 16 determines whether smart battery communication is being received from a battery that is currently being monitored. If smart battery communication is not being received, the microprocessor proceeds to a point B, which will be described in more detail below with reference to FIG. 4, and if smart battery communication is being received, the microprocessor proceeds to a decision block 222.

At decision block 222, the microprocessor determines whether the smart battery has communicated a zero capacity or fault indication. If such a communication has been received, the microprocessor proceeds to a block 224, and if such a communication has not been received, the microprocessor proceeds to a decision block 226.

At block 224, the microprocessor is set to operate as though communication with the smart battery has been lost, but sets a flag to periodically recheck to see if communication from the smart battery has been restored. From block 224, the microprocessor proceeds to point B, which will be described in more detail below with reference to FIG. 4.

At decision block 226, the microprocessor determines whether the communication received from the smart battery gives an indication of a low battery condition. If a low battery condition is indicated, the microprocessor proceeds to a block 228, and if a low battery condition is not indicated, the microprocessor returns to decision block 220 and battery monitoring is continued. At block 228, if a low battery condition is detected, the microprocessor indicates to the user that a low battery condition has been detected and, then, proceeds to a point C, which will be described in more detail below with reference to FIG. 5.

FIG. 4 illustrates the continuing battery monitoring operation of FIG. 3, when either a non-smart battery is being monitored or a smart battery with no communication is being monitored. As shown in FIG. 4, from a point B, the microprocessor continues to a block 230 which indicates that a non-smart battery or a smart battery with no communication is being monitored. At a decision block 232, the microprocessor determines if the unit has first been powered on and, if it is, runs a load test. A suitable load test consists of placing a 1.5 amp load on each battery for 200 milliseconds and then checking at the end of 200 milliseconds to see if the battery voltage is less than or equal to 10.5 volts. This test is an especially important criterion in a defibrillator due to the high current and charging requirement that a power source must meet to avoid interruption or delay of critical defibrillator functions. If the load test is not passed, i.e., the battery voltage is less than or equal to 10.5 volts, the microprocessor proceeds to a block 234. If the load test is passed, i.e., the battery voltage is greater than 10.5 volts, the microprocessor proceeds to a decision block 236.

At decision block 234, within a predetermined short period of time, i.e., two seconds, a low battery is detected by the microprocessor and a message is displayed to a user. The microprocessor then proceeds to point C, which will be described in more detail below with reference to FIG. 5.

At decision block 236, the microprocessor determines whether the sensed battery voltage during normal operation after the initial power on of the system is less than or equal to some predetermined value, e.g., 8.28 volts for one sample period (in the one actual embodiment of the invention, one sample period is 56 microseconds). If the voltage is less than the predetermined value, e.g., 8.28 volts, the microprocessor proceeds to a block 238, and if the voltage is not less than 8.28 volts, the microprocessor proceeds to a decision block 240. At block 238, the microprocessor determines that the end of battery reserve has been detected for the battery. Thereafter, the routine proceeds to point A of FIG. 3 and battery monitoring is continued.

At decision block 240, the microprocessor determines whether the sensed battery voltage during normal operation is less than or equal to some predetermined value, e.g., 10.5 volts +/− some predetermined percent, e.g., 5% for a predetermined period of time, e.g., one second. If the sensed battery voltage is less than the predetermined value for the predetermined period of time, the microprocessor proceeds to block 234. If the sensed battery voltage is not less than the predetermined value for the predetermined period of time, the microprocessor returns to point A and battery monitoring continues.

FIG. 5 illustrates the battery monitoring routine as it continues once a low battery indication has been determined by the microprocessor. Continuing from point C, the microprocessor proceeds to block 250 where a low battery indicator is activated. The low battery indicator remains activated until one of the conditions of FIG. 5 is met. The defibrillator supports a low battery indicator and message for each battery.

At a decision block 252, the microprocessor determines if the defibrillator has been turned off. If the defibrillator has been turned off, the microprocessor proceeds to a block 262 where the low battery indicator is deactivated. If the defibrillator has not been turned off, the microprocessor proceeds to a decision block 254.

At decision block 254, the microprocessor determines if power has been removed from the defibrillator. If power has been removed from the defibrillator, the microprocessor proceeds to block 262. If power has not been removed from the defibrillator, the microprocessor proceeds to a decision block 256.

At decision block 256, the microprocessor determines if low battery voltages have caused the defibrillator to turn off. If low battery voltages have caused the defibrillator to turn off, the microprocessor proceeds to block 262. If low battery voltages have not caused the defibrillator to turn off, the microprocessor proceeds to a decision block 258.

At decision block 258, the microprocessor determines whether the battery has been removed. If the battery has been removed, the microprocessor proceeds to block 262. If the battery has not been removed, the microprocessor proceeds to a decision block 260.

At decision block 260, the microprocessor determines whether the defibrillator is coupled to AC power or to AC power through an auxiliary power supply. If the unit is coupled to AC power, the microprocessor proceeds to block 262. If the unit is not coupled to AC power, the microprocessor proceeds to point A and battery monitoring continues.

Figure 6:
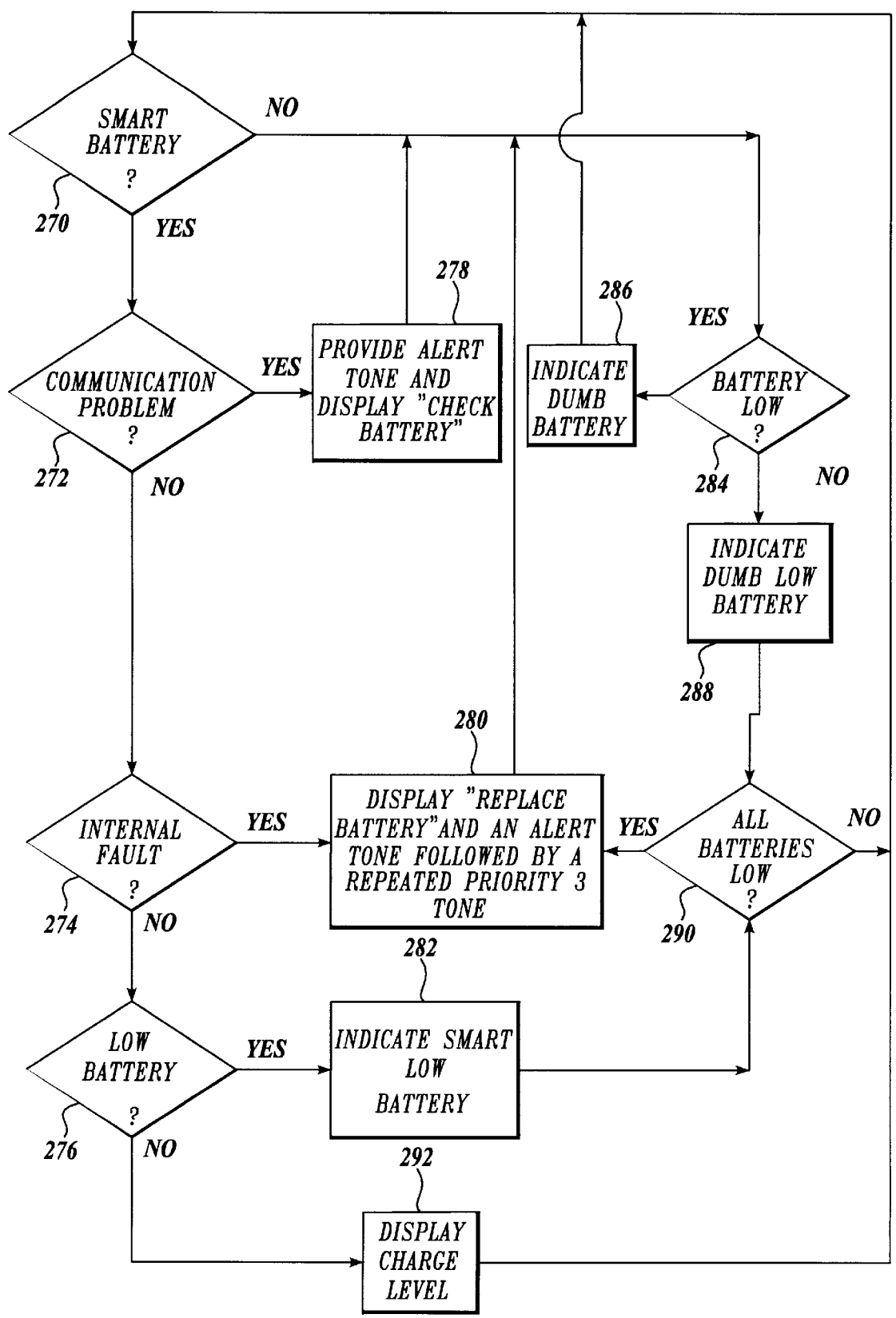
FIG. 6 is a flow chart illustrating a method for generally displaying information to a user of the device.

FIG. 6 illustrates the general method of displaying to a user the various battery conditions and faults that are determined by the microprocessor. As shown in a decision block 270, the microprocessor determines that the battery that is being monitored is a smart battery. As described next, if the battery is a smart battery, the microprocessor proceeds with checking the battery for errors through a series of steps prior to displaying the charge level of the battery. If the microprocessor determines that the battery that is being monitored is a smart battery, the microprocessor proceeds to a decision block 272. If the microprocessor determines that the battery that is being monitored is not a smart battery, the microprocessor proceeds to a decision block 284.

At decision block 272, the microprocessor determines whether there is a communication problem with the smart battery. If a communication problem exists, the microprocessor proceeds to a block 278 and, if a communication problem does not exist, the microprocessor proceeds to a decision block 274. At block 278, the microprocessor causes an alert tone to be emitted by the defibrillator and the display to display a "check battery" message. The microprocessor then proceeds to a decision block 284. Thereafter, the smart battery is treated as a non-smart or dumb battery, as described in more detail below.

At decision block 274, the microprocessor determines whether an internal battery fault has been detected and communicated by the smart battery. If an internal fault has been communicated, the microprocessor proceeds to a block 280 and, if an internal fault has not been detected, the microprocessor proceeds to a decision block 276. At block 280, the microprocessor causes the display to display a "replace battery" message and the defibrillator to produce an alert tone. The alert tone is followed by another tone designated a repeated priority 3 tone. The microprocessor then proceeds to decision block 284.

At decision block 276, the microprocessor determines whether the smart battery has communicated that it has a low battery condition. If a low battery condition has been communicated, the microprocessor proceeds to a block 282, and if a low battery condition has not been indicated, the microprocessor proceeds to a block 292. At block 282, the microprocessor causes the display to display a "smart low battery" icon. The microprocessor then proceeds to a decision block 290, which is described below.

At block 292, the microprocessor causes the display to display the charge level of the smart battery. In one actual embodiment of the invention, the charge level is displayed as a type of "fuel gauge" that shows increasing power by displaying from zero to four lighted bars. If the smart battery indicates that it has greater than 75% of its maximum charge level, four bars are displayed. If the smart battery indicates that its charge level is less than or equal to 75% and greater than 50% of its maximum charge level, then three bars are displayed. If the smart battery indicates that its charge level is less than or equal to 50% but greater than 25% of its maximum charge level, then two bars are displayed. If the smart battery indicates that its charge level is less than or equal to 25% but greater than 0% of its maximum charge level, then one bar is displayed. If the smart battery indicates that its charge level is less than or equal to 0% of its maximum charge level, then zero bars are displayed. From block 292, the microprocessor returns to decision block 270 and monitoring continues.

As described above, the microprocessor reaches decision block 284 when the battery is to be evaluated as a non-smart or dumb battery, or if a smart battery has communication or internal fault problems. At decision block 284, a test is made to determine if the output voltage of the battery is above or below a predetermined low battery threshold. If the output voltage of the battery is determined to be below the low battery threshold, the microprocessor proceeds to a block 288 and, if the output of the battery is determined to not be below the low battery threshold, the microprocessor proceeds to a block 286. At block 286, the microprocessor causes the display to display a "dumb battery" icon. From block 286, the microprocessor returns to decision block 270 and monitoring continues.

At block 288, the microprocessor causes the display to display a "dumb low battery" icon. From block 288, the microprocessor proceeds to decision block 290. At decision block 290, the microprocessor determines if all of the batteries in the system are low. If all of the batteries are determined to be low, the microprocessor proceeds to block 280 and, if all of the batteries are not low, the microprocessor returns to decision block 270 and monitoring continues.

One of the primary advantages of the above-described system is that the user need not be concerned with what the power source is and when to switch, as the system takes care of these considerations and prompts the user if action is needed. The above routines also keep a user completely informed as to the status of the device. This is extremely advantageous in a defibrillator, because the timing for providing potentially life saving defibrillation pulses is very important, and concerns about power supply maintenance could distract a user. Keeping a user informed is also important because inattentiveness can possibly render a defibrillator inoperable.

Another advantage over older systems is that the unit can be upgraded via software changes as battery technology changes. In addition, the invention is advantageous in that its system can make use of the new "smart batteries" that provide internal measurements through a serial communication bus. The unit can also combine battery technology and can use both older non-smart batteries and smart batteries in a single system. This is especially advantageous in defibrillators, where special battery packs are often used, and the expense or non-availability of certain types of battery packs may make combined usage a requirement. Also, the system can coordinate battery charging and usage with an external power supply, when one is made available.

Another advantage of the present invention is that the power sources are switched and fused to a single common system power line 150, requiring fewer unit wires carrying large currents. Another advantage is that the electronic switching avoids the electromechanical failures of manual switches.

While the preferred embodiment of the invention has been illustrated and described, it will be appreciated that various changes can be made therein without departing from the spirit and scope of the invention.

What is claimed is:

1. A power supply switching circuit for use in a portable external defibrillator, said portable external defibrillator being operable for generating defibrillation pulses, the power supply switching circuit comprising:

an output;

a plurality of power sources;

a plurality of power supply ports, each port configured to receive one of said power sources, wherein said plurality of power sources are at least one of external power sources or batteries, wherein said batteries are at least one of smart batteries or dumb batteries, said smart batteries including monitoring devices, and said dumb batteries not including monitoring devices;

a plurality of microprocessor controllable switches for selectively coupling the power supply ports to the output of the power supply switching circuit;

a microprocessor connected to said plurality of power supply ports and to said plurality of microprocessor controllable switches, the microprocessor acquiring data regarding said power sources, said microprocessor processing the data regarding said power sources; and a control program for controlling the operation of said microprocessor, the control program including a set of criteria that are desired for the operation of the external defibrillator and a selection routine for selecting a power supply port to be coupled to the output of the power supply switching circuit, the selection routine evaluating the data regarding the power sources according to the criteria that are desired for the operation of the external defibrillator, the selection routine including a subroutine suitable for evaluating the data regarding the smart battery power sources and for determining a set of smart batteries that are capable of powering the external defibrillator, and from the set of smart batteries selecting the best smart battery according to the criteria that are desired for the operation of the external defibrillator.

2. The power supply switching circuit of claim 1, wherein the power sources comprise at least one dumb battery and the data that is acquired regarding the power sources includes data regarding the dumb battery, and wherein the selection routine also includes a second subroutine suitable for evaluating the data regarding the dumb battery power sources.

3. The power supply switching circuit of claim 2, including a plurality of monitoring lines for connecting said plurality of power supply ports to said microprocessor.

4. The power supply switching circuit of claim 3, wherein said smart batteries include communication terminals and said power sources include power terminals, and further wherein said plurality of power supply ports each include power terminal ports for connection to the power terminals of the power sources, and at least some of said plurality of power supply ports include communication terminal ports for connection to the communication terminals of smart batteries and wherein said monitoring lines are connected to said power terminal ports and said communication terminal ports.

5. The power supply switching circuit of claim 4, further comprising a display, the display being coupled to the microprocessor.

6. The power supply switching circuit of claim 5, wherein the microprocessor monitors, through the monitoring lines, the condition of batteries that are being used as power sources, the condition of the batteries indicating when the batteries are in need of maintenance or charging, and causes the display to display the condition of the batteries including an indication when the batteries are in need of maintenance or charging.

7. The power supply switching circuit of claim 5, wherein the microprocessor monitors, through the monitoring lines, the capacity of any batteries that are being used as power sources, and causes the display to display a gauge that is indicative of the capacity of said batteries being used as power sources.

8. The power supply switching circuit of claim 1, wherein the external power source is a smart external power source, the microprocessor including a charging subroutine that coordinates battery charging by the smart external power source, the smart external power source including a monitoring device.

9. The power supply switching circuit of claim 1, further comprising a load circuit coupled to one other batteries, the voltage output of the battery being measured by the microprocessor, wherein the selection routine also includes a testing subroutine for detecting the criteria that are desired for the operation of the external defibrillator, the testing subroutine including a test for one of the batteries under which the load circuit is used to place a load on the battery to draw an estimated current from the battery, and after a predetermined period of time the voltage output of the battery is measured by the microprocessor to see if the voltage falls within a selected range.

10. The power supply switching circuit of claim 8, wherein one of the batteries is coupled to the output of the power supply switching circuit, and wherein the battery that is coupled to the output of the power supply switching circuit produces an estimated current that is greater than or equal to 1.5 amps.

11. The power supply switching circuit of claim 1, wherein the microprocessor controllable switches are solid state switches.

12. A power switching circuit comprising an output and a plurality of power sources, the power switching circuit for use in a portable electronic device and automatically switching power in the portable electronic device between the plurality of power sources, the portable electronic device having criteria established for selecting power sources, the output of the power switching circuit being coupled to the power sources, wherein said plurality of power sources are at least one of external power sources or batteries, wherein said batteries are at least one of smart batteries or dumb batteries, said smart batteries including monitoring devices, and said dumb batteries not including monitoring devices, the power switching circuit further comprising:

(a) a plurality of power supply ports, each port for coupling to and receiving power from one of said power sources;

(b) a power output for providing power to the portable electronic device;

(c) a plurality of switches for selectively connecting the power supply ports to the power output; and (d) a microprocessor that is programmed to select the best available power source according to the criteria established for the portable electronic device, said microprocessor coupled to said power supply ports and to said plurality of switches for:

(i) automatically monitoring said plurality of power supply ports to determine the presence and status of power sources when said power sources are coupled to said plurality of power supply ports, said automatic monitoring including determining the presence of said external power source and the status of both smart and dumb batteries; and (ii) determining if batteries are in a low battery condition and selecting the best available power source for said portable electronic device based on criteria established for the portable electronic device, including selecting the best battery from a plurality of batteries that are determined to not be in a low battery condition by the microprocessor; and (iii) controlling said plurality of switches to switch the power supply port associated with the selected best available power source to be connected to said power output.

13. The power switching circuit of claim 12, wherein said smart batteries include communication terminals and at least some of said plurality of power supply ports include communication ports for communication to the communication terminals of said smart batteries and wherein said microprocessor is coupled to said communication ports.

14. The power switching circuit of claim 12, wherein the microprocessor detects the existence of predetermined selection criteria associated with the related best available power source, and the best available power source selected by the microprocessor is used as the power source by the portable electronic device until the microprocessor detects the existence of the predetermined selection criteria associated with the selected best available power source and wherein said microprocessor selects another available power source when the existence of said predetermined selection criteria is detected.

15. The power switching circuit of claim 12, wherein selection of the best available power source by the microprocessor includes a determination of when the output of batteries included in said power sources is less than or equal to a first threshold voltage for a predetermined sample period.

16. The circuit of claim 12, wherein the microprocessor senses the output voltage of the batteries and the selection of the best available power source by the microprocessor includes deciding that one of said batteries included in said power sources has been fully used by the microprocessor sensing the output voltage of the battery for a predetermined sample period and determining that the output voltage is less than or equal to a threshold voltage for said predetermined sample period, and then selecting a different power source than said battery.

17. A method for providing automatic power switching in a portable electronic device, the portable electronic device including input ports for receiving power sources such as batteries and external power sources, the portable electronic device also including a microprocessor coupled to the power sources and to a series of switches for evaluating the power sources and for selectively coupling the power sources to the power input of the portable electronic device, the method comprising:

(a) determining if an external power source is available and, if it is, using the external power source as the power source for the portable electronic device;

(b) if an external power source is not available, determining what batteries are available and their status; and (c) of the available batteries, evaluating the batteries to determine the best battery according to a predefined criteria; and (d) using the best battery as the power source for the portable electronic device until the predefined criteria of the battery reaches a low level that defines a switching point, at which time a different power source is used.

18. The method of claim 17, wherein the portable electronic device is a defibrillator and the predefined criteria that is used to select the best battery is based on the particular operating characteristics of the defibrillator.

19. The method of claim 18, wherein the criteria used to evaluate the batteries depends at least upon the depletion level of the battery.

20. The method of claim 18, wherein when an external power source is available, the method includes charging of the batteries using the external power source.

21. The method of claim 18, wherein the method includes evaluating both power sources that include a monitoring system, and power sources that do not include a monitoring system.

22. The method of claim 21, including the defibrillator providing an indication to a user of the status of the batteries and including providing to the user an indication that a battery that does not include a monitoring system has reached a low battery condition when the sensed output voltage of the battery is less than or equal to a first threshold for a predetermined sample period.

23. The method of claim 22, including providing to a user an indication that a battery that does not include a monitoring system has reached the end of battery reserve when the sensed battery voltage is less than or equal to a second threshold for a predetermined sample period.

24. A method for operating a power supply switching circuit, the power supply switching circuit being for use in a portable external defibrillator, said portable external defibrillator being operable for generating defibrillation pulses, the power supply switching circuit comprising:

an output;

a plurality of power sources;

a plurality of power supply ports, each port configured to receive one of said power sources, wherein said plurality of power sources are at least one of external power sources or batteries, wherein said batteries are at least one of smart batteries or dumb batteries, said smart batteries including monitoring devices, and said dumb batteries not including monitoring devices;

a plurality of microprocessor controllable switches for selectively coupling the power supply ports to the output of the power supply switching circuit;

a microprocessor connected to said plurality of power supply ports and to said plurality of microprocessor controllable switches;

the method comprising:

establishing a set of criteria that are desired for the operation of the external defibrillator;

using said microprocessor to acquire data regarding the power sources;

establishing a selection routine for selecting a power source to be coupled to the output of the power supply switching circuit, the selection routine evaluating the data regarding the power sources according to the criteria that are desired for the operation of the external defibrillator, the selection routine including a subroutine suitable for evaluating the data regarding the smart battery power sources and for determining a set of smart batteries that are capable of powering the external defibrillator, and from the set of smart batteries selecting the best smart battery according to the criteria that are desired for the operation of the external defibrillator.

25. The method of claim 24, wherein the predefined criteria that is used to select the best battery is based on the particular operating characteristics of the defibrillator.

26. The method of claim 25, wherein the criteria used to evaluate the batteries depends at least upon the depletion level of the battery.

27. The method of claim 24, wherein when an external power source is available, the method includes charging of the batteries using the external power source.

28. The method of claim 24, wherein the method includes evaluating both power sources that include a monitoring system, and power sources that do not include a monitoring system.

29. The method of claim 28, including the defibrillator providing an indication to a user of the status of the batteries and including providing to the user an indication that a battery that does not include a monitoring system has reached a low battery condition when the sensed output voltage of the battery is less than or equal to a first threshold for a predetermined sample period.

30. The method of claim 29, including providing to a user an indication that a battery that does not include a monitoring system has reached the end of battery reserve when the sensed battery voltage is less than or equal to a second threshold for a predetermined sample period.

* * * * *

UNITED STATES PATENT AND TRADEMARK OFFICE
CERTIFICATE OF CORRECTION

PATENT NO. : 6,223,077 B1
DATED : April 24, 2001
INVENTOR(S) : S.O. Schweizer et al.

It is certified that error appears in the above-identified patent and that said Letters Patent is hereby corrected as shown below:

<u>Title page,</u>
Primary Examiner, "Evanlsko" should read -- Evanisko --

<u>Column 14, claims 17-21,</u>
Lines 33-67, delete in their entirety, renumbering subsequent claims and dependencies accordingly <u>Column 15, claims 22-23,</u>
Lines 1-12, delete in their entirety, renumbering subsequent claims and dependencies accordingly Signed and Sealed this Twenty-second Day of January, 2002

Attest:

Attesting Officer

JAMES E. ROGAN
*Director of the United States Patent and Trademark Office*